United States Patent
Finlayson

[11] Patent Number: 5,885,227
[45] Date of Patent: Mar. 23, 1999

[54] FLEXIBLE GUIDEWIRE WITH RADIOPAQUE PLASTIC TIP

[75] Inventor: Maureen Finlayson, Acton, Mass.

[73] Assignee: Radius Medical Technologies, Inc., Acton, Mass.

[21] Appl. No.: 824,004

[22] Filed: Mar. 25, 1997

[51] Int. Cl.$^6$ .................................................. A61B 5/00
[52] U.S. Cl. ............................................................. 600/585
[58] Field of Search ..................................... 128/772, 656, 128/657, 658; 604/264, 265, 280, 282; 600/585, 433, 434, 435

[56] References Cited

U.S. PATENT DOCUMENTS

| | | | |
|---|---|---|---|
| 4,721,117 | 1/1988 | Mar et al. | 128/772 |
| 4,953,553 | 9/1990 | Tremulis | 128/637 |
| 5,243,996 | 9/1993 | Hall | 128/772 |
| 5,253,653 | 10/1993 | Daigle et al. | 128/772 |
| 5,345,945 | 9/1994 | Hodgson et al. | 128/772 |
| 5,429,597 | 7/1995 | DeMello et al. | 604/49 |
| 5,433,200 | 7/1995 | Fleischhacker, Jr. | 128/657 |
| 5,439,000 | 8/1995 | Gunderson et al. | 128/664 |
| 5,549,580 | 8/1996 | Diaz | 604/280 |
| 5,551,444 | 9/1996 | Finlayson | 600/585 |
| 5,596,996 | 1/1997 | Johanson et al. | 600/585 |

FOREIGN PATENT DOCUMENTS

| | | |
|---|---|---|
| 0519604A2 | 12/1992 | European Pat. Off. . |
| 08257136 | 10/1996 | Japan . |
| WO92/14508 | 9/1992 | WIPO . |
| WO95/31244 | 11/1995 | WIPO . |

*Primary Examiner*—Max Hindenburg
*Assistant Examiner*—Charles Marmor, II
*Attorney, Agent, or Firm*—Cesari and McKenna, LLP

[57] ABSTRACT

A guidewire includes (i) a tapered core; (ii) an elongated non-radiopaque coil that is coincident with the core and extends over a distal portion of the core up to a proximal portion of a tapered end section of the core; and (iii) a radiopaque plastic tip that fits over the distal end of the core. The proximal end of the plastic tip may extend over the distal end of the non-radiopaque coil. The tip may then be attached to the coil by forcing the proximal end of the tip through the windings at the distal end of the coil. The distal end of the plastic tip extends slightly beyond the distal end of the core, to form a deformable bumper. The outer diameter of the proximal end of the plastic tip is the same as the outer diameter of the coil, which is the same diameter as proximal end of the core before its first taper. Accordingly, the guidewire has an essentially uniform outer diameter over its entire length. The durometer hardness of the plastic material used to form the tip may be adjusted, to alter the stiffness of the tip. Thus, the tip may be made stiffer or more flexible without changing the outer dimensions of the guidewire. The tip may also be tapered, as desired, to narrow the outer diameter of the distal end of the guidewire. A low friction coating may be added to the wire, to facilitate movement of the wire through the arteries.

19 Claims, 4 Drawing Sheets

FLEXIBLE GUIDEWIRE WITH RADIOPAQUE PLASTIC TIP

FIELD OF THE INVENTION

This invention relates generally to guidewires for directing a catheter or other medical instrument through the cardiovascular system and, more particularly, to guide wires that have radiopaque distal ends.

BACKGROUND OF THE INVENTION

Guidewires for use in, for example, percutaneous transluminal coronary artery angioplasty (PTCA), must be thin and flexible enough to advance through small arteries within the coronary vasculature. These wires must also be sturdy enough to be manipulated from the outside of the body, such that a distal end of the wire can be brought into contact with a selected region of the coronary artery. Further, they must be strong enough to survive a "pull test" without breaking, to ensure that they do not come apart in the body.

Prior known guidewires each essentially include a solid tapered core and an elongated non-radiopaque coil or sleeve that is coincident with and extends over a distal portion of the core. The coil or sleeve adds strength to the tapered distal end of the core, essentially without limiting its flexibility. Each of the guidewires also has radiopaque material at its distal end. This allows the cardiologist to observe, using x-ray or fluoroscopy, the progress of the wire through the arteries. The remainder of the wire is non-radiopaque, to avoid obscuring the arteries from view.

One type of prior known guidewire includes a shorter radiopaque end coil that is attached to the distal end of the elongated non-radiopaque coil. The two coils have the same outer diameter and are typically made from coil wires that have the same thickness. The elongated coil is made from a material, such as stainless steel, which is relatively inexpensive. The shorter radiopaque coil is made from a precious metal, such as platinum, and is thus relatively expensive, even though it is fairly short.

A problem with this guidewire, beyond the expense of the radiopaque coil, is that it is difficult to assemble. The distal end of the elongated coil and the proximal end of the shorter coil must be held completely flush while they are welded or soldered together, to ensure a strong joint. Since these coils are each approximately 0.014 inch in diameter, it is difficult to hold them in proper alignment during the welding or soldering operation. There is also a danger that the two coils may become unattached during use. If this happens, the radiopaque coil may slide off the end of the essentially smooth core and become free in a patient's body.

Another type of known guidewire has small bands of radiopaque material wrapped around a non-radiopaque sleeve that covers the distal end of the wire. One of the problems with this guidewire is that the bands are so small that they are difficult to discern under x-ray or fluoroscopy. Accordingly, this guidewire may be difficult to use.

Another problem with the band-wrapped guidewire is that it is relatively expensive to manufacture. The assembly process necessarily includes the steps of wrapping the small bands around the wire and securing them to the wires such that the bands cannot be pulled off during use. The steps associated with attaching the bands to the guidewire are in addition to the conventional steps involved in guidewire manufacture.

SUMMARY OF THE INVENTION

The invention is a guidewire that includes (i) a tapered center core with a proximal end and a tapered end section that includes a flattened distal end, (ii) a coincident elongated non-radiopaque coil that extends over a distal portion of the core up to a proximal portion of the tapered end section of the core, and (iii) a relatively short radiopaque plastic tip that fits over the distal end of the core. The radiopaque plastic tip has an outer diameter that is essentially the same as the coil, which is typically 0.014 inch, and thus, can be readily seen under x-ray or fluoroscopy.

The plastic tip is made radiopaque by blending radiopaque materials, such as bisimuth, barium, tungsten, platinum, tantalum and so forth with the plastic material. The durometer hardness of the plastic material can be tailored to provide desired tip stiffness, without altering the dimensions of the tip.

More specifically, the current guidewire includes a solid wire core that tapers at several points along its length to its flattened distal end. The elongated non-radiopaque coil attaches at its proximal end to the core, preferably at the core's first taper. The coil attaches at its distal end to a proximal portion of the tapered end section of the core. The ends of the coil are joined to the core through soldering, welding or brazing.

The plastic tip in one embodiment is slightly oversized and is placed such that its proximal end fits over the distal end of the non-radiopaque coil. The plastic tip is then heated, under compression, to shrink the tip and force the material at the proximal end of the tip between the windings of the distal end of the coil. This forms a smooth transition between the coil and the tip, and results in a guidewire with a uniform diameter over its entire length. Adhesive may also be applied to the inside of the plastic tip or to the outside of the tapered end of the core, to promote a strong bond between the tip and the core.

In an alternative embodiment, the distal end of the coil may be tapered, as necessary, to ensure a uniform outer diameter at the transition between the tip and the coil. The tip may also be tapered, to produce a guidewire with a strong, tapered end.

The proximal end of the radiopaque plastic tip may be slightly flared, so that the end fits easily over the distal end of the coil. The plastic material at the end is forced through the windings of the coil, as discussed above, to form between the coil and the tip a smooth transition that has a uniform diameter.

The plastic tip may instead be affixed to the coil and the core with adhesive.

In any of these arrangements, the distal end of the plastic tip preferably extends slightly beyond the distal end of the core, to form a deformable, atraumatic "bumper." Thus, there is no need to attach a separate end piece.

The radiopaque plastic tip, at least at its proximal end, has the same outer diameter as the non-tapered end of the coil. Accordingly, the tip is readily seen in x-rays or fluoroscopy.

The guidewire may be coated with a teflon, silicon, hydrophylic or other low friction coating, to allow the wire to slide more easily through the arteries. As discussed below, the coating coats all but the plastic tip, and thus, extends nearly to the end of the guidewire.

BRIEF DESCRIPTION OF THE DRAWINGS

The above and further advantages of the invention may be better understood by referring to the following description in conjunction with the accompanying drawings, in which.

DETAILED DESCRIPTION OF AN ILLUSTRATIVE EMBODIMENT

Figure 1:
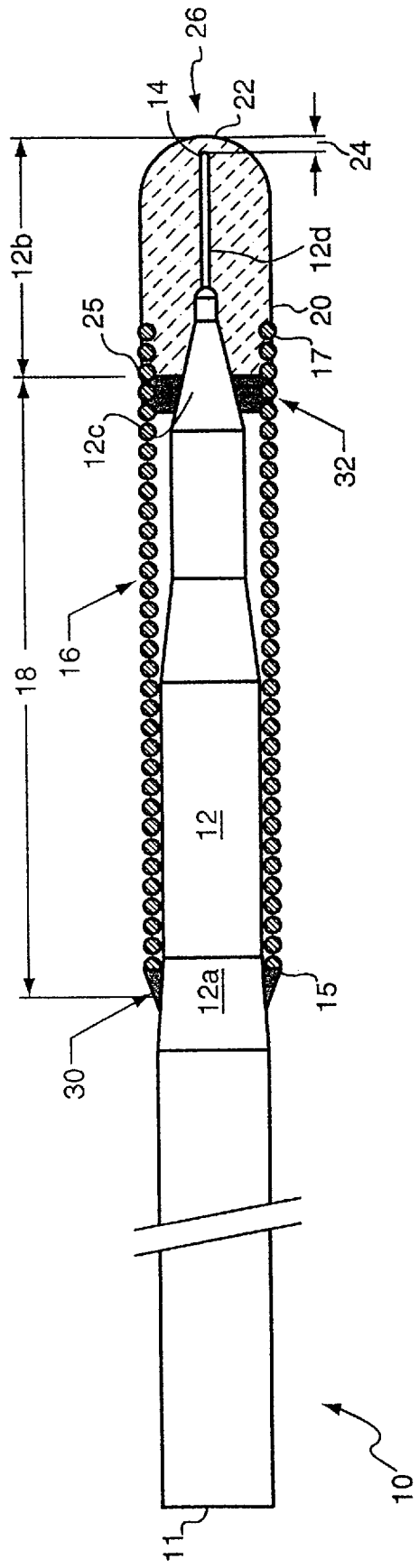
FIG. 1 is a cross-sectional view of a guidewire with a radiopaque plastic tip, which is constructed in accordance with the invention.

FIG. 1 depicts in cross section a flexible guidewire 10 that includes a core 12, which is tapered to an essentially flattened section 12d at its distal end 14. An elongated non-radiopaque coil 16 is coincident with and extends over a distal portion 18 of the core 12, up to and slightly beyond the proximal end 12c of a tapered end section 12b of the core 12. A radiopaque plastic tip 20 is coincident with the distal end of the non-radiopaque coil 16. The tip extends over the tapered end section 12b of the core, to form a distal end 26 of the guidewire 10. The distal end 22 of the plastic tip 20 extends slightly beyond the distal end 14 of the core by approximately 1 millimeter and forms a soft, atraumatic bumper 24.

The outer diameter of the radiopaque plastic tip 20 is the same as the outer diameter of the coil, which, in turn, is the same as the outer diameter of the core 12 before its first taper 12a. The guidewire 10 thus has an essentially uniform outer diameter from its proximal end 11 to its distal end 26.

The plastic tip 20 is made radiopaque by blending with the plastic material radiopaque materials such as bisimuth, barium, tungsten, platinum, tantalum and so forth. The durometer hardness of the plastic material can be adjusted in a known manner, to alter the stiffness of the distal end 26 of the wire 10. Thus, the end 26 may be made stiffer or more flexible without altering the outer dimensions of the wire.

The non-radiopaque coil 16 attaches at its proximal end 15 to the first tapered section 12a of the core 12. The coil 16 may be attached to this section by, for example, welding, brazing, or soldering, as depicted in the drawing by joint 30. The coil attaches near its distal end 17 to the proximal end 12c of the tapered end section 12b of the core 12 also by welding, brazing or soldering, as depicted by joint 32.

The radiopaque plastic tip 20 attaches to the distal ends of the coil 16 and the core 12. In this arrangement, the tip 20 is preferably slightly oversized, so that it can be heated and shrunk under compression, to form the end 26 of guidewire shown in FIG. 1.

To attach the radiopaque plastic tip at the end of the core, the oversized tip is placed over the distal end of the core, with the proximal end 25 of the tip overlapping the distal end 17 of the coil 16. Then, heat is applied along with a compressing force, to soften the distal end of the tip slightly and force the softened plastic material through the windings of the coil 16. This results in a smooth transition with uniform diameter, between the coil 16 and the plastic tip 20. The guidewire thus has uniform diameter from its proximal end 11 to its distal end 26.

An adhesive may also be applied to the interior of the plastic tip 20 or to the outside of the end section 12b of the core prior to the heating. The adhesive then forms a strong bond between the tip 20 and the core 12.

Figure 2:
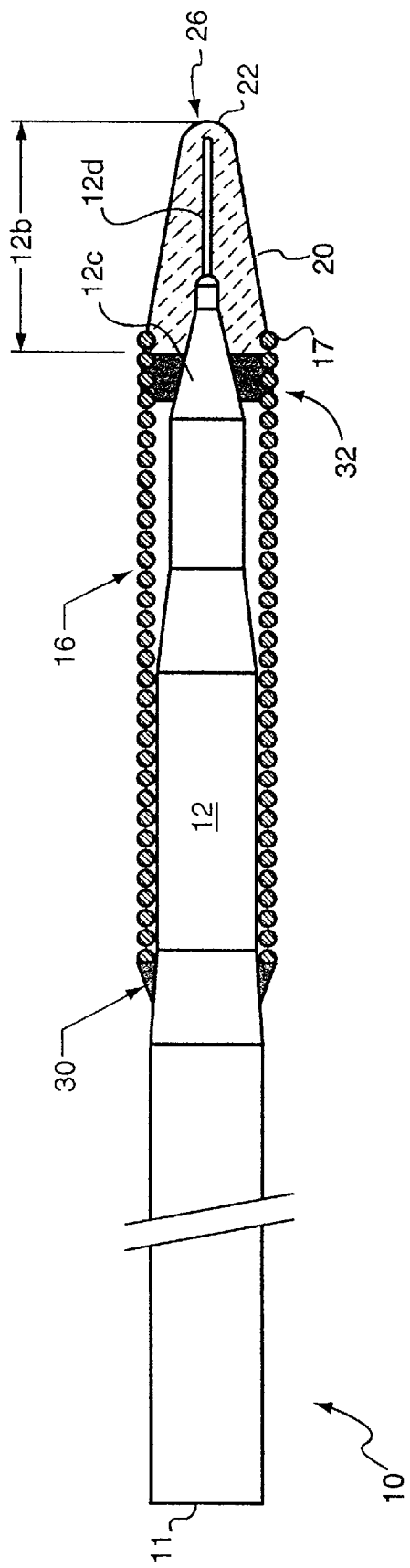
FIG. 2 is a cross-sectional view of the guidewire of FIG. 1, with a tapered radiopaque plastic tip.

As discussed above, the end section 12d of the core may be flattened. To make a corresponding end portion of the guidewire readily bendable, such that a cardiologist may shape the end section 12d, as necessary, to facilitate the movement of the wire along a selected artery. As depicted in FIG. 2, the plastic tip 20 may also be tapered, to reduce the outer diameter of the distal end 26 of the guidewire 10.

Figure 3:
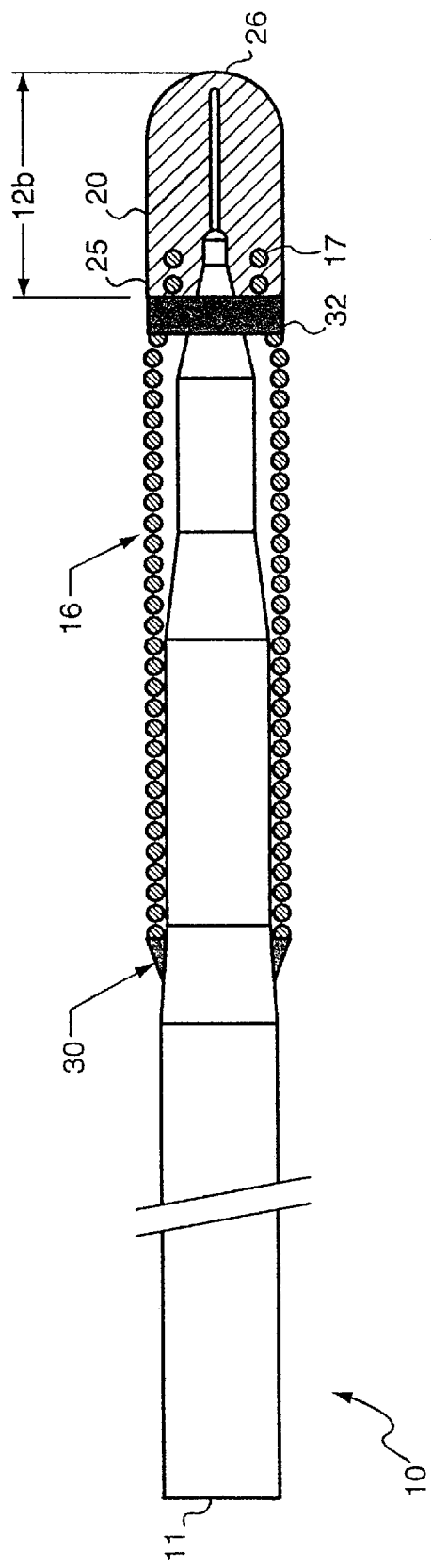
FIG. 3 is a cross-sectional view of the guidewire of FIG. 1, with a tapered non-radiopaque coil.

Referring also to FIG. 3, the distal end of the coil 16 may be tapered. In such an arrangement, the tip 20 may have the same diameter as the proximal end 11 of the guidewire, or the tip 20 may also be tapered (FIG. 2). The tapered coil may facilitate a smooth transition between the coil and the tip, particularly if the tip is flared at its proximal end, as discussed below.

Figure 4:
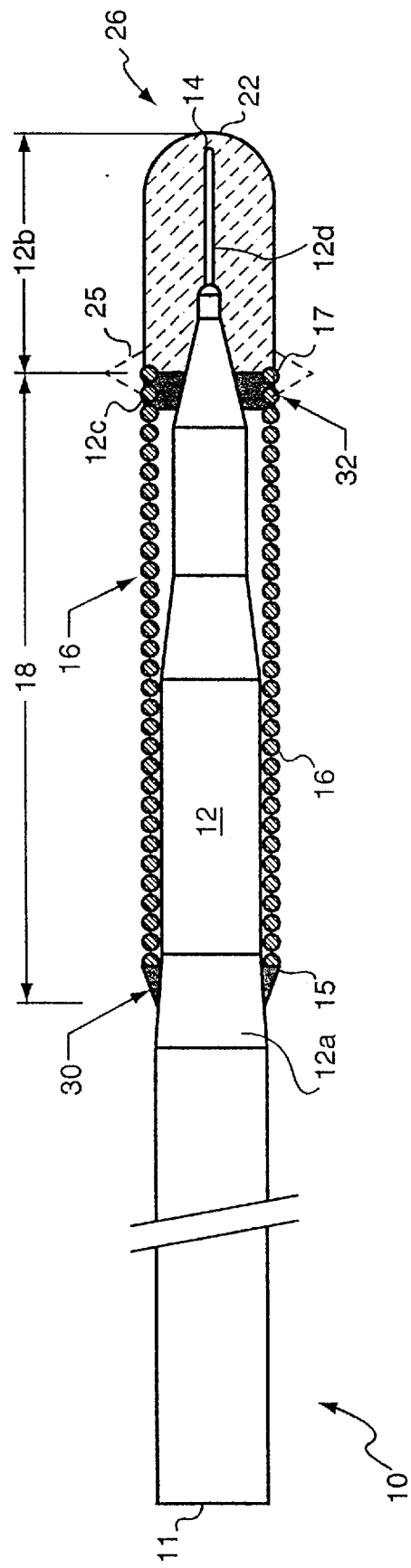
FIG. 4 is a cross-sectional view of the guidewire of FIG. 1, with the radiopaque plastic tip attached by adhesive.

As depicted in FIG. 4, the plastic tip 20 may instead be attached to the coil 16 and the core 12 solely by adhesive.

The proximal end 25 of the tip 20 may be slightly flared as indicated by dotted lines in the drawing, such that it fits easily over the distal end of the coil 16. The flared end also provides additional material to force through the windings of the coil, as depicted in FIGS. 1–3, to produce a strong joint between the coil and the tip.

The guidewire 10 may be coated with a silicon, teflon, hydrophilic or other low friction coating. This allows the wire to slide more easily through the artery. If the coating is teflon, its cure temperature exceeds the melting temperature of the plastic tip, and thus, the coating stops at the proximal end 17 of the outer coil 20. Accordingly, the teflon coating can be applied up to the plastic tip, that is, nearly to the distal end 26 of the guidewire, to within approximately 1 to 3 centimeters of the end of the guidewire.

Table 1 sets forth the dimensions of an exemplary embodiment of the guidewire 10. In this exemplary embodiment the guidewire 10 has an overall outer diameter of 0.014 inch. The radiopaque plastic tip has the same outer diameter, at least at its proximal end, and is approximately 3 centimeters in length, and thus, can be readily seen under x-ray and fluoroscopy.

The guidewire 10, in any of its embodiments, is easy to assemble. An assembler slides the coil 16 over the distal portion of the tapered core 12 until the proximal end of the coil is stopped by the first taper 12a of the core. The assembler then joins both the proximal end and the distal end of the coil to the core by soldering, brazing or welding. The assembler next fits the plastic tip over the tapered end section 12b of the core, until the proximal end of the tip overlaps the distal end of the coil. He then attaches the tip to the core with either adhesive or a combination of melt forming and adhesive, as discussed above. The plastic tip extends slightly beyond the flattened end 12d of the core 12, to form the bumper 24. Accordingly, a separate rounded end piece need not be attached. This method of assembly is easier than that used to assemble the type of guidewires in which the non-radiopaque elongated coil and a radiopaque end coil must be held with their adjacent ends flush while they are soldered or welded together.

The foregoing description has been limited to a specific embodiment of this invention. It will be apparent, however, that variations and modifications may be made to the invention, with the attainment of some or all of its advantages. Therefore, it is the object of the appended claims to cover all such variations and modifications as come within the true spirit and scope of the invention.

TABLE 1

Dimensions of Exemplary Embodiment

| | |
|---|---|
| Core Outer Diameter | .014 inch |
| Overall Guidewire Length | 180 cm |

TABLE 1-continued

Dimensions of Exemplary Embodiment

| | |
|---|---|
| Overall Core Taper Length | 30 cm |
| Core Taper Length (Flattened End) | 1.5 cm |
| Core Taper Outer Diameter (Flattened End) | .002 inch |
| Non-Radiopaque Coil Length | 27 cm |
| Non-Radiopaque Outer Diameter | .014 inch |
| Radiopaque Plastic Tip Length | 3 cm |
| Radiopaque Tip Outer Diameter | .014 inch |

What is claimed is:

1. A guidewire for use in gaining access to an artery, the guidewire including:
   A. a tapered core with a proximal end and a tapered distal end section that includes a proximal portion and a distal portion;
   B. an elongated non-radiopaque coil that is concentric with the core and extends over a distal portion of the core to the proximal portion of the tapered distal end section, the coil having a proximal end and a distal end; and
   C. a radiopaque plastic tip having a proximal end and a distal end, the tip fitting over the distal portion of the tapered distal end section of the core with the proximal end of the tip overlapping the distal end of the coil.

2. The guidewire of claim 1 wherein the distal end of the radiopaque plastic tip extends beyond the distal end of the core and forms a deformable end.

3. The guidewire of claim 1, wherein the radiopaque plastic tip attaches to the coil by being forced through windings of the distal end of the coil.

4. The guidewire of claim 3, wherein the radiopaque plastic tip further attaches to the core by adhesive.

5. The guidewire of claim 4 wherein the radiopaque plastic tip includes a flared proximal end that fits over the distal end of the coil.

6. The guidewire of claim 3 wherein the radiopaque plastic tip is tapered from the proximal end to the distal end.

7. The guidewire of claim 3 wherein the distal end of the radiopaque plastic tip extends beyond the distal end of the core and forms a deformable end.

8. The guidewire of claim 6 wherein the distal end of the radiopaque plastic tip extends beyond the distal end of the core and forms a deformable end.

9. The guidewire of claim 1, wherein the guidewire is coated with a low friction coating.

10. The guidewire of claim 1 wherein the distal portion of the tapered distal end section of the core includes a flattened section.

11. A guidewire for use in gaining access to an artery, the guidewire including a proximal end and a distal end, wherein the distal end of the guidewire is formed from:
   A. a tapered distal end section of a tapered core wire, the tapered distal end section including a proximal portion and a distal portion;
   B. a distal end of a non-radiopaque coil that is concentric with the core wire and covers a portion of the tapered distal end section of the core wire; and
   C. a radiopaque plastic tip that covers the distal portion of the tapered distal end section of the core wire and provides a smooth transition for the distal end of the coil.

12. The guidewire of claim 11 wherein the radiopaque plastic tip tapers.

13. The guidewire of claim 12 wherein each of the coil and the proximal end of the radiopaque plastic tip has an outer diameter that is the same as the outer diameter of a proximal end of the core wire.

14. The guidewire of claim 11 wherein the plastic tip has a distal end and a proximal end and the proximal end of the tip overlaps the distal end of the coil.

15. The guidewire of claim 14, wherein the radiopaque plastic tip attaches to the distal end of the coil by having material at the proximal end of the tip forced through windings of the coil.

16. The guidewire of claim 15 wherein the tip further attaches to the core wire by adhesive.

17. The guidewire of claim 16, wherein the radiopaque plastic tip extends beyond the tapered distal end section of the core wire, to form a deformable end.

18. The guidewire of claim 17 wherein the guidewire is coated with a low friction coating.

19. The guidewire of claim 14, wherein the proximal end of the radiopaque plastic tip is flared, to fit over the distal end of the coil.

* * * * *